United States Patent [19]

Macri

[11] Patent Number: 5,100,806
[45] Date of Patent: Mar. 31, 1992

[54] METHOD FOR DETECTING EDWARDS SYNDROME

[76] Inventor: James N. Macri, 170 Sidney St., Oyster Bay, N.Y. 11771

[21] Appl. No.: 328,383

[22] Filed: Mar. 24, 1989

[51] Int. Cl.$^5$ .................. G01N 33/543; C12Q 1/68
[52] U.S. Cl. .................................. 436/518; 435/6; 436/818
[58] Field of Search .............. 436/501, 536, 547, 548, 436/87, 818, 518; 435/6

[56] References Cited

U.S. PATENT DOCUMENTS 4,804,626  2/1989  Bellet et al. .................. 436/548
4,874,693  10/1989  Bogart ........................... 436/548

OTHER PUBLICATIONS

Canick et al., Amer. J. Human Genetics 45 (4 Suppl.): A255, 1989.
Johnson et al., Amer. J. Human Genetics 45 (4 Suppl.): A261, 1989.

*Primary Examiner*—Esther L. Kepplinger
*Assistant Examiner*—Donna C. Wortman
*Attorney, Agent, or Firm*—Kenyon & Kenyon

[57] ABSTRACT

A method for determining if a pregnant woman is at significant risk of carrying a fetus with Edwards syndrome comprising measuring the pregnant woman's maternal blood levels of the free beta subunit of human chorionic gonadotropin.

1 Claim, No Drawings

METHOD FOR DETECTING EDWARDS SYNDROME

BACKGROUND OF THE INVENTION

The present invention relates to a method for detecting fetal Edwards syndrome (Trisomy 18) during prenatal screening. More particularly the present invention relates to a method for improving detection efficiency in screening for Edwards syndrome by measuring the amount of the free beta subunit of human chorionic gonadotropin (hCG) in the blood of pregnant women.

Edwards syndrome, also referred to as trisomy 18, is a cause of severe mental retardation. Generally, fetal Edwards syndrome can be determined by a diagnostic procedure including amniocentesis and karyotyping. However, this diagnostic procedure is invasive and involves risk to the woman and the fetus. Amniocentesis and karyotyping are not routinely performed during all pregnancies. Instead, one or more screening methods may be utilized to determine when the risk to the pregnancy warrants the risk of undergoing an invasive diagnostic procedure.

Historically, the prenatal search for chromosomal abnormalities has focused on pregnant women at and over the age of 35, at which age the risks of chromosomal abnormalities in the fetus approach or exceed the risks of diagnostic procedures utilized to detect fetal chromosomal abnormalities. Therefore the standard method of prenatal screening has involved selecting women for diagnostic amniocentesis on the basis of maternal age. Age, however, is an inadequate screening criterion in that only about 5% of all Edwards syndrome pregnancies can be detected by carrying out amniocentesis and karyotyping on the 5% of pregnant women most at risk, that is, those aged 35 years or greater. And, because in actual clinical practice only about half of the women aged 35 years or greater undergo amniocentesis and karyotyping, fewer than 2.5% of Edwards syndrome pregnancies are prenatally detected.

I have discovered a previously unknown association between lowered levels of maternal blood free beta-hCG and fetal Edwards syndrome. A screening method using the maternal blood level of free beta hCG will vastly improve the detection efficiency of Edwards syndrome. Detection efficiency refers to the percentage of cases of fetal Edwards syndrome which are correctly detected for a chosen cut off level. The cut off level will be more fully explained in a following section. These and other discoveries will be more fully explained in the Summary of the Invention section and the Detailed Description of the Invention section.

One object of the present invention is to provide a method and process for screening for fetal Edwards syndrome which detects a greater percentage of fetal Edwards syndrome cases for a given false positive rate than other known prenatal screening methods.

Another object of the present invention is to provide a method and process for screening for fetal Edwards syndrome which has a lesser false positive rate for a given detection percentage than other known methods.

A still further object of the present invention is to provide a method and process for screening for fetal Edwards syndrome by measuring the level of maternal blood free beta-hCG.

Other objects and advantages of the present invention will become apparent in the following description of the invention.

SUMMARY OF THE INVENTION

To achieve these and other objects, according to the present invention a pregnant woman's (hereinafter the patient) maternal blood level of free beta-hCG is measured by conventional analytical methods which can include generally known immunoassay techniques and other techniques known in the art. Low levels of free beta-hCG, or no free beta-hCG, indicate the patient has an increased risk of carrying a fetus with Edwards syndrome. As will be understood by those of ordinary skill in the art, to improve detection efficiency the level of free beta-hCG may be compared to a set of reference data to determine the patient's risk of carrying a fetus with Edwards syndrome.

An advantage of the present invention is that it correctly predicts a higher percentage of fetal Edwards syndrome case, with a lesser false positive rate, than other known methods and processes.

Other advantages of the present invention will become clear from the following more detailed description and the following example.

DETAILED DESCRIPTION OF THE INVENTION

In one embodiment of the present invention a maternal blood sample is taken from a patient. The maternal blood level of free beta-hCG is then measured by a conventional analytical methods, such as immunological methods known to the art. For example, the maternal blood level of free beta-hCG may be measured by a radioimmunoassay, such as the free beta-hCG radioimmunoassay commercially available from BIOMERICA, 1533 Monrovia Ave., Newport Beach, Calif. 92663. As will be understood by those of ordinary skill in the art, the present invention is not limited to the use of a free beta-hCG radioimmunoassay, such as the one available from BIOMERICA, but encompasses any conventional analytical method for measuring the maternal blood level of free beta-hCG.

Levels of free beta-hCG below about 1 ng/ml (nanogram per milliliter), or no free-beta hCG, indicate the patient has an increased risk of carrying a fetus with Edwards syndrome.

To improve detection efficiency the maternal blood level of free beta-hCG may be compared to a set of reference data to determine whether the patient is at an increased risk of carrying a fetus with Edwards syndrome. Although any of the known analytical methods for measuring the maternal blood level of free beta-hCG will function in the present invention, as obvious to one skilled in the art, the analytical method used for free beta-hCG must be the same method used to generate the reference data for free beta-hCG. If a new immunological method is used for free beta-hCG, a new set of reference data, based on data developed with the method, must be generated.

The reference data reflects the maternal blood level of free beta-hCG for pregnant women carrying fetuses with Edwards syndrome (also referred to as "affected") and/or the maternal blood level of free beta-hCG for pregnant women carrying normal fetuses (also referred to as "unaffected"). As will be generally understood by those of skill in the art, methods for screening for fetal Edwards syndrome are processes of decision making by comparison. For any decision making process, reference values based on patients having the disease or condition of interest and/or patients not having the disease or condition of interest are needed. In the present invention the reference values are the maternal blood level of free beta-hCG, in both pregnant women carrying Edwards syndrome fetuses and pregnant women carrying normal fetuses. A set of reference data is established by collecting the reference values for a number of samples. As will be obvious to those of skill in the art, the set of reference data will improve by including increasing numbers of reference values.

To determine whether the patient is at increased risk of carrying a fetus with Edwards syndrome a cut-off must be established. This cut-off may be established by the laboratory, the physician or on a case by case basis by each patient. The cut-off level can be based on several criteria including the number of women who would go on for further invasive diagnostic testing, the average risk of carrying an Edwards syndrome fetus of all the women who go on for further invasive diagnostic testing, a decision that any woman whose patient specific risk is greater than a certain risk level such as 1 in 365 should go on for further invasive diagnostic testing, or other criteria known to those skilled in the art.

The average risk of carrying an Edwards syndrome fetus can be calculated from the following formula:

$$\frac{D*R}{(D*R) - F(1 - R)}$$

where
D = Detection Efficiency
R = Prior Risk
F = False Positive

The cut-off level -could be established using a number of methods, including: percentiles, mean plus or minus standard deviation(s); multiples of median value; patient specific risk or other methods known to those who are skilled in the art.

The effectiveness and advantages of the present invention will be further illustrated by the following example.

EXAMPLE

Over 500 patient samples were utilized to study the relationship of fetal Edwards syndrome to the maternal blood levels of free beta-hCG, 7 samples from pregnant women known to be carrying fetuses with Edwards syndrome and 542 unaffected samples. All samples were from singleton, non-diabetic, white gravid women.

For each sample the level of free beta-hCG was determined by the free beta-hCG radioimmunoassay commercially available from BIOMERICA, 1533 Monrovia Ave., Newport Beach, Calif. 92663. We observed that 3.9% of the unaffected pregnancies had level of the free beta subunit of hCG below 1 ng/ml while 85.7% of the affected cases had a level of the free beta subunit of hCG below 1 ng/ml. The average risk for patients who had a level below 1 ng/ml was 1 in 274.

The data confirms our discovery that the free beta-hCG subunit contributes a higher detection efficiency for Edwards syndrome than any known means of screening for Edwards syndrome.

I claim:

1. A method for screening a pregnant woman to determine whether said pregnant woman is carrying a fetus with Edwards syndrome comprising:
immunologically measuring the pregnant woman's blood level of free beta human chorionic gonadotropin (HCG);
determining the pregnant woman's gestational age; and
comparing the measured blood level of free beta HCG and the woman's gestational age to a cut-off level based on reference values of: 1) levels of free beta HCG, measured by the same method, in pregnant women carrying normal fetuses at the same gestational age and 2) levels of free beta HCG, measured by the same method, in pregnant women carrying fetuses with Edwards syndrome at the same gestational age, wherein a decreased level of beta HCG in said pregnant woman, with respect to said cut-off level, is indicative of a positive screening result.

* * * * *